US008354269B2

(12) United States Patent
Simpson et al.

(10) Patent No.: US 8,354,269 B2
(45) Date of Patent: Jan. 15, 2013

(54) OPTIMISED MEDIA CONTAINING NICKEL FOR FERMENTATION OF CARBONMONOXIDE

(75) Inventors: Sean Dennis Simpson, Auckland (NZ); Ian Lindstrand Warner, Auckland (NZ); Jennifer Mon Yee Eung, Auckland (NZ); Michael Kopke, Auckland (NZ)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/058,375

(22) PCT Filed: Nov. 30, 2009

(86) PCT No.: PCT/NZ2009/000267
§ 371 (c)(1),
(2), (4) Date: Aug. 18, 2011

(87) PCT Pub. No.: WO2010/064932
PCT Pub. Date: Jun. 10, 2010

(65) Prior Publication Data
US 2011/0294177 A1  Dec. 1, 2011

Related U.S. Application Data

(60) Provisional application No. 61/119,018, filed on Dec. 1, 2008, provisional application No. 61/159,784, filed on Mar. 12, 2009, provisional application No. 61/160,673, filed on Mar. 16, 2009.

(51) Int. Cl.
C12P 7/54 (2006.01)
C12P 7/08 (2006.01)
A62D 3/02 (2007.01)
A61L 9/01 (2006.01)

(52) U.S. Cl. ...... 435/266; 435/140; 435/163; 435/262.5
(58) Field of Classification Search ............ 435/140, 435/163, 262.5, 266
See application file for complete search history.

(56) References Cited

U.S. PATENT DOCUMENTS

| 4,021,579 A | 5/1977 | Barrett |
| 5,100,553 A | 3/1992 | Nomura et al. |
| 5,173,429 A | 12/1992 | Gaddy et al. |
| 5,593,886 A | 1/1997 | Gaddy |
| 5,807,722 A | 9/1998 | Gaddy |
| 5,821,111 A | 10/1998 | Grady et al. |
| 5,861,137 A | 1/1999 | Edlund |
| 6,136,577 A | 10/2000 | Gaddy |
| 6,340,581 B1 | 1/2002 | Gaddy |
| 6,368,819 B1 | 4/2002 | Gaddy et al. |
| 6,425,401 B1 | 7/2002 | Williams |
| 6,605,376 B2 | 8/2003 | Verykios |
| 6,737,257 B2 | 5/2004 | Blum |
| 6,753,170 B2 | 6/2004 | Gaddy et al. |
| RE39,175 E | 7/2006 | Gaddy et al. |
| 7,078,201 B2 | 7/2006 | Burmaster |
| 7,196,218 B2 | 3/2007 | Gaddy et al. |
| 7,285,402 B2 | 10/2007 | Gaddy et al. |
| 2003/0211585 A1 | 11/2003 | Gaddy et al. |
| 2005/0266540 A1 | 12/2005 | Offerman et al. |
| 2006/0252137 A1 | 11/2006 | Burmaster |
| 2007/0275447 A1 | 11/2007 | Lewis et al. |
| 2008/0057554 A1* | 3/2008 | Huhnke et al. ............ 435/161 |
| 2010/0323417 A1 | 12/2010 | Simpson et al. |

FOREIGN PATENT DOCUMENTS

| CN | 1433718 | 8/2003 |
| EP | 0085757 A1 | 8/1983 |
| EP | 0 117 309 | 12/1983 |
| JP | 61-205478 | 9/1986 |
| JP | 62-091293 | 4/1987 |
| JP | 02312584 A * | 12/1990 |
| JP | 2003-135088 | 5/2003 |
| WO | 98/00558 | 1/1998 |
| WO | 00/68407 | 11/2000 |
| WO | 02/08438 | 1/2002 |
| WO | 2005/118826 | 12/2005 |
| WO | 2006/108532 | 10/2006 |
| WO | 2007/064545 | 6/2007 |
| WO | 2007/117157 | 10/2007 |
| WO | 2008/028055 | 3/2008 |
| WO | 2008/115080 | 9/2008 |
| WO | 2008/154301 | 12/2008 |
| WO | 2009/020747 | 2/2009 |
| WO | 2009/022925 | 2/2009 |
| WO | 2009/058028 | 5/2009 |
| WO | 2009/064200 | 5/2009 |
| WO | 2009/064201 | 5/2009 |
| WO | 2009/113878 | 9/2009 |
| WO | 2010/064933 | 6/2010 |
| WO | 2010/093262 | 8/2010 |
| WO | 2010/098679 | 9/2010 |
| WO | 2011/002318 | 1/2011 |

OTHER PUBLICATIONS

Diekert et al "Nickel requirement for carbon monoxide Dehydrogenase Formation in *Clostridium pasteurianum*" Archives of Microbiology (1979) 122, 117-120.*

Phillips, J.R., et al. "Synthesis Gas a Substrate for the Biological Production of Fuels and Chemicals." Applied Biochemistry and Biotechnology, 1994, 45/46. pp. 145-157.

Abrini, Jamal et al. "*Clostridium autoethanogenum*, sp. nov., an anaerobic bacterium that produces ethanol from carbon monoxide." Archives of Microbiology, vol. 161, 1994, pp. 345-351.

Ragsdale, S.W. "Life with Carbon Monoxide." Critical Reviews in Biochemistry and Molecular Biology, 2004, 39, pp. 165-195.

(Continued)

Primary Examiner — Jon P Weber
Assistant Examiner — Charles Zoltan Constantine
(74) Attorney, Agent, or Firm — Frank S Molinaro

(57) ABSTRACT

The invention relates to improvements in the production of alcohols by microbial fermentation, particularly to production of alcohols by microbial fermentation of substrates comprising CO. It more particularly relates to the provision of an improved fermentation media, comprising nickel, to a fermentation system such that one or more micro-organisms convert a substrate comprising CO to one or more alcohols, such as ethanol. In particular embodiments, a microbial culture is provided with at least 10 μM nickel, such that CO uptake by the microbial culture increases and ethanol productivity improves.

20 Claims, No Drawings

OTHER PUBLICATIONS

Henstra, et al. "Microbiology of Synthesis Gas Fermentation for Biofuel Production." Current Opinion in Biotechnology, 2007, 18, pp. 200-206.

Najafpour, Ghasem; Younsei, Habibollah. "Ethanol and acetate synthesis from waste gas using batch culture of *Clostridium ljungdahlii*." Enzyme and Microbial Technology, 2006, vol. 38(1-2), pp. 223-228.

Pusheva, M.A. et al. "The effect of nickel on the metabolism of homoacetogenic bacteria." Mikrobiologiya (1989), 58(2), 206-11.

* cited by examiner

US 8,354,269 B2

OPTIMISED MEDIA CONTAINING NICKEL FOR FERMENTATION OF CARBONMONOXIDE

CROSS REFERENCE TO RELATED APPLICATIONS

This application is a National Stage of International Application No. PCT/NZ2009/000267 filed on Nov. 30, 2009, which claims the benefit of the priority date of the following: U.S. Provisional Application No. 61/119,018 filed Dec. 1, 2008; U.S. Provisional Application 61/159,784 filed Mar. 12, 2009 and U.S. Provisional Application 61/160,673 filed Mar. 16, 2009. The contents of the prior applications mentioned above are incorporated herein by reference.

FIELD OF THE INVENTION

This invention relates generally to methods for increasing the efficiency of microbial growth and production of products, such as alcohols and acids by microbial fermentation. More particularly the invention relates to processes for producing alcohols, particularly ethanol, by microbial fermentation of substrates containing carbon monoxide.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to continue to grow sharply in the future, due to an increased interest in ethanol in Europe, Japan, the USA and several developing nations.

For example, in the USA, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, or as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, and the cultivation of starch or sucrose-producing crops for ethanol production is not economically sustainable in all geographies. Therefore, it is of interest to develop technologies to convert lower cost and/or more abundant carbon resources into fuel ethanol.

CO is a major free energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al, Archives of Microbiology 161, pp 345-351 (1994)).

Several enzymes known to be associated with the ability of micro-organisms to use carbon monoxide as their sole source of carbon and energy are known to require metal co-factors for their activity. Examples of key enzymes requiring metal cofactor binding for activity include carbon monoxide dehydrogenase (CODH), and acetyl —CoA synthase (ACS).

WO2007/117157, WO2008/115080, WO2009/022925, WO2009/058028, WO2009/064200, WO2009/064201 and WO2009/113878, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process. WO2009/022925 discloses the effect of pH and ORP in the conversion of substrates comprising CO to products such as acids and alcohols by fermentation. WO2009/058028 describes the use of industrial waste gases for the production of products, such as alcohol, by fermentation. WO2009/064201 discloses carriers for CO and the use of CO in fermentation. WO2009/113878 discloses the conversion of acid(s) to alcohol(s) during fermentation of a substrate comprising CO.

Microbes capable of growing on CO-containing gases are known to do so at a slower rate than is traditionally associated with microbes grown on sugars. From a commercial perspective, in a fermentation process the time required for a microbial population to grow to a sufficiently high cell density to allow an economically viable level of product to be synthesised, is a key operating cost affecting the profitability of the process. Technologies that act to enhance culture growth rates and therefore reduce the time required for cell populations to reach high cell densities may serve to improve the commercial viability of the overall process.

In fermentation processes dedicated to the production of alcohols from gas feedstocks, ensuring that the appropriate metal co-factors are present in the correct concentrations may be critical to maintaining optimal alcohol productivities. Furthermore, given the large volumes of media used in many industrial fermentation processes, the cost of media components may also influence the profitability of a process. Therefore, identifying the necessary trace metal co-factors for alcohol production and optimising co-factor concentrations required in fermentation systems using carbon monoxide containing gases as a feedstock, is a key component in ensuring high alcohol production rates and low process operating costs.

Ethanol production by micro-organisms by fermentation of gases is typically associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions. Other waste products, such as butyric acid/butyrate may also be produced during commonly used fermentation processes.

It is well known that acids such as acetate can have an inhibitory effect on alcohol production by a microbial culture. As such, a fermentation process should desirably maintain acids at a low level.

It is an object of the present invention to provide a process that goes at least some way towards overcoming the above disadvantages, or at least to provide the public with a useful choice.

SUMMARY OF THE INVENTION

A method of improving efficiency of microbial fermentation of a substrate comprising CO, the method including providing nickel to one or more micro-organisms such that CO uptake increases.

In another broad aspect, the invention provides a method of maintaining or increasing efficiency of microbial fermentation of a substrate comprising CO, the method comprising the step of maintaining the concentration of nickel in a reaction broth above a desired concentration.

In particular embodiments of the first and second aspects, a substrate comprising CO is converted into metabolites such as acid(s) and/or alcohol(s) by a microbial culture. In particular embodiments, efficiency is maintained or increased by increasing CO uptake of the microbial culture.

In certain embodiments of the first and second aspects, increasing CO uptake increases growth rate and/or growth levels of the microbial culture. Additionally or alternatively, increasing CO uptake increases metabolite productivity and/or metabolite production. In certain embodiments of the invention, alcohol production is substantially increased. Typically, alcohol production is substantially increased while acetate production remains constant or decreases. In particular embodiments, alcohol is a major product of the fermentation reaction with an alcohol:acid ratio greater than 10:1; or at least 20:1; or at least 30:1; or at least 50:1; or at least 100:1.

In particular embodiments, alcohol is produced substantially without acid production.

In another broad aspect, the invention provides a method for producing alcohols by fermentation of a substrate comprising CO by a microbial culture, the method including increasing CO uptake of the microbial culture. In particular embodiments, the method includes adding nickel to the microbial culture. In particular embodiments, alcohol is produced with little or no acetate production.

In another broad aspect, the present invention provides a method of producing one or more acid and/or alcohol by microbial fermentation, the method comprising the steps of:

(a) providing a substrate containing carbon monoxide, carbon dioxide and/or hydrogen;
(b) in a bioreactor containing a culture of one or more micro-organisms anaerobically fermenting the substrate to produce one or more products consisting of acids and/or alcohols;

wherein nickel is provided to the culture such that acid(s) production and/or alcohol(s) production is enhanced.

In particular embodiments, the nickel is provided at a desired concentration of at least 10 µM; or at least 50 µM; or at least 100 µM; or at least 500 µM; or at least 1 mM; or at least 3 mM. Nickel can be provided to a liquid nutrient media comprising nutrients suitable to support microbial growth and/or product biosynthesis at concentrations of at least 2.5 mg/L; or at least 10 mg/L; or at least 100 mg/L; or at least 500 mg/L. In particular embodiments, the nickel is maintained at a concentration of at least 2.5 mg/L/gram dry weight of microbial cells; or at least 10 mg/L/g; or at least 100 mg/L/g; or at least 500 mg/L/g. In particular embodiments, the concentration of nickel is maintained above a desired level by adding a predetermined amount of nickel to the culture at a predetermined time.

In particular embodiments, nickel is added to the culture or bioreactor in the form of one or more salt of nickel. Salts include nickel chloride, nickel sulphate, nickel carbonate or nickel acetate. In particular embodiments, nickel is added in the form of a composition comprising nickel with one or more diluents, carriers and/or other ingredients.

In certain embodiments of the invention, before adding the nickel, the methods also comprise the steps of:
(a) taking a sample of the culture which may be contained within the bioreactor; and
(b) measuring the concentration of nickel, the alcohol and/or acid produced, and/or microbial cell density, wherein the predetermined amount and predetermined time are calculated from the microbial cell density and/or the concentration of alcohol and/or acid and/or the concentration of nickel.

In certain embodiments, the substrate is gaseous and comprises a gas obtained as a by-product of an industrial process. In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing. Preferably, the gaseous substrate comprises a gas obtained from a steel mill.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

In various embodiments, the fermentation is carried out using a culture of one or more strains of carboxydotrophic bacteria. In various embodiments, the carboxydotrophic bacterium is selected from *Clostridium, Moorella, Oxobacter, Peptostreptococcus, Acetobacterium, Eubacterium* or *Butyribacterium*. In one embodiment, the carboxydotrophic bacterium is *Clostridium autoethanogenum*. In another embodiment, the carboxydotrophic bacterium is *Clostridium*

*carboxydivorans*. In another embodiment, the carboxydotrophic bacterium is *Clostridium ljungdahlii*.

In yet another broad aspect, the invention provides a nutrient media adapted to support microbial fermentation, the media comprising nickel at a concentration of at least 10 µM and one or more diluents and/or carriers. In particular embodiments the nickel concentration is at least 50 µM; or at least 100 µM; or at least 500 µM; or at least 1 mM; or at least 3 mM. In particular embodiments, the nickel is provided in a liquid nutrient medium at a concentration of at least 2.5 mg/L/gram dry weight of microbial cells; or at least 10 mg/L/g; or at least 100 mg/L/g; or at least 500 mg/L/g.

In another embodiment of the invention, nickel is provided in a liquid nutrient medium comprising at least Fe, Co and/or Zn. In particular embodiments, the nickel is provided such that the Ni:Fe ratio is at least 1:2; or at least 1:1; or at least 2:1; or at least 5:1; or at least 10:1; or at least 50:1; or at least 100:1. In certain embodiments, the metals and/or co-factors are provided such that the Ni:Co ratio is at least 1:1; or at least 2:1; or at least 5:1; or at least 10:1; or at least 50:1; or at least 100:1. In certain embodiments, the metals and/or co-factors are provided such that the Ni:Zn ratio is at least 1:1; or at least 2:1; or at least 5:1; or at least 10:1; or at least 50:1; or at least 100:1.

In other embodiments of the invention the methods may be used to produce hydrogen.

Although the invention is broadly as defined above, it is not limited thereto and also includes embodiments of which the following description provides examples.

DETAILED DESCRIPTION OF THE INVENTION

It is recognised that the CO uptake ability (or rate of CO uptake) of carboxydotrophic micro-organisms correlates to the growth rate and/or rate of product biosynthesis. In accordance with the methods of the invention, the CO uptake rate of a carboxydotrophic microbial culture has been increased. As a result of increasing CO uptake rate, the growth rate and/or product biosynthesis increases. In accordance with particular embodiments of the invention, one or more co-factors, such as nickel, or one or more nickel salts, can be added to a microbial culture comprising carboxydotrophic micro-organisms to improve or enhance CO uptake by the culture.

Nickel salts are commonly added to a carboxydotrophic microbial culture to support microbial growth and/or product biosynthesis. However, it has been surprisingly recognised that known media recipes do not contain enough nickel, and this may limit the rate at which CO can be utilised by a microbial culture. Without wishing to be bound by theory, it is well known that the CODH/ACS enzymatic system in particular carboxydotrophic bacteria, such as *Clostridium autoethanogenum* contains nickel co-factors. In accordance with the methods of the invention, the operation of the CODH/ACS enzymatic system can be enhanced by providing additional co-factors, such as nickel salts. It is recognised that the concentration of nickel provided in accordance with the methods of the invention may be substantially larger than the amount required in CODH/ACS enzymes. However, by way of example, elevated levels of nickel in a liquid nutrient medium enhance CO uptake.

In particular embodiments, growth rate and/or total growth of a microbial culture can be substantially improved by providing additional nickel to the culture. Additionally, or alternatively, metabolite production rates and/or total metabolite production by the microbial culture can also be substantially increased.

In particular embodiments of the invention, the alcohol productivity rate and/or total alcohol production is substantially increased while acid production remains negligible. Without wishing to be bound by theory, it is considered that the additional reducing equivalents available from increased CO uptake allows a microbial culture to reduce acids, such as acetate, such that acids substantially do not accumulate in the fermentation broth. As such, in particular embodiments of the invention, there is provided a method of producing alcohols while maintaining low levels of acids in a fermentation broth. In another embodiment, there is provided a method of producing alcohols in the absence of acids, wherein nickel is added to the fermentation broth at a level higher than is normal.

In certain embodiments, nickel is provided in a novel nutrient medium. In particular embodiments, the novel nutrient medium also comprises at least Fe, Co and/or Zn.

The invention may be readily applicable to fermentation reactions which utilise substrates other than carbon monoxide, produce alcohols other than ethanol, and utilise micro-organisms other than *Clostridium autoethanogenum*, *Clostridium ljungdahlii* and *Clostridium carboxydivorans*.

DEFINITIONS

Unless otherwise defined, the following terms as used throughout this specification are defined as follows:

The terms "increasing the efficiency", "increased efficiency" and the like, when used in relation to a fermentation process, include, but are not limited to, increasing one or more of: the rate of growth of micro-organisms catalysing the fermentation, the volume of desired product (such as alcohols) produced per volume of substrate (such as carbon monoxide) consumed, the rate of production or level of production of the desired product, and the relative proportion of the desired product produced compared with other by-products of the fermentation.

The term "co-substrate" refers to a substance that while not being the primary energy and material source for product synthesis, can be utilised for product synthesis when added in addition to the primary substrate.

The use of term "acid", "acids" and the like when referring to adding an "acid" to a culture or bioreactor in accordance with the invention should be taken broadly, including any monocarboxylic and dicarboxylic acids. In addition reference to addition of "acids(s)" should be taken to include reference to the equivalent salt or a mixture of salt and acid. Similarly, references to specific acids herein should be taken to include reference to equivalent salts (for example butyric acid and butyrate) and vice versa. The ratio of molecular acid to carboxylate in the fermentation broth is dependent upon the pH of the system. Exemplary acids include acetic acid, propionic acid, n-butyric acid, n-pentanoic acid, n-hexanoic acid, and benzoic acid.

The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "substrates comprising carbon monoxide" include any solid, liquid or gaseous material containing CO that may be introduced into a bioreactor for fermentation. "Gaseous substrates comprising carbon monoxide" include any gas which contains carbon monoxide. The gaseous substrate will typically contain a substantial proportion of CO, such as, for example, at least about 15% to about 95% CO by volume.

As will be appreciated from the description provided herein after, the words "metal", "metals" and the like, should be taken to include metal ions and salts as the context requires.

The term "co-factor" and the like include chemical compounds, metals or ions, that interact with enzymes and assist in the function of the enzyme. Typically, co-factors are often classified as inorganic substances that are required for, or increase the rate of, enzymatic catalysis.

The invention provides methods for increasing the efficiency of microbial fermentation processes and methods for increasing the growth of micro-organisms used in the fermentation process. These methods involve utilising an improved nutrient or growth media in the fermentation reaction or supplementing the media during the fermentation process.

While the following description focuses on a preferred embodiment of the invention, namely the production of ethanol and/or acetate using CO as the primary substrate, it should be appreciated that the invention may be applicable to production of alternative alcohols and/or acids and the use of alternative substrates as will be known by persons of ordinary skill in the art to which the invention relates. For example, gaseous substrates containing carbon dioxide and hydrogen may be used. Further, the invention may be applicable to fermentation to produce butyrate, propionate, caproate, ethanol, propanol, and butanol. The methods may also be of use in producing hydrogen. By way of example, these products may be produced by fermentation using microbes from the genus *Moorella*, *Clostridia*, *Ruminococcus*, *Acetobacterium*, *Eubacterium*, *Butyribacterium*, *Oxobacter*, *Methanosarcina*, *Methanosarcina*, and *Desulfotomaculum*.

Fermentation Reaction

The invention has particular applicability to supporting the production of ethanol from gaseous substrates such as high volume CO-containing industrial flue gases. In some embodiments of the invention, the substrate comprising CO is derived from carbon containing waste, for example, industrial waste gases or from the gasification of other wastes. As such, the methods of the invention represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing. The invention is also applicable to reactions which produce alternative alcohols.

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acids such as acetic acid, and are suitable for use in the process of the present invention. Examples of such bacteria that may be suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091), *Clostridium ragsdalei* (WO/2008/028055) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Moorella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp41-65). In addition, it should be understood that other carboxydotrophic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061. Another exemplary micro-organism is *Clostridium ljungdahlii*. In one embodiment, the *Clostridium ljungdahlii* is a *Clostridium ljungdahlii* having the identifying characteristics of DSMZ deposit number DSMZ 13528. Another exemplary micro-organism is *Clostridium carboxydivorans*. In one embodiment, the *Clostridium carboxydivorans* is a *Clostridium carboxydivorans* having the identifying characteristics of DSMZ deposit number DSMZ 15243.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J.

L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as a continuous stirred tank reactor (CSTR), an immobilised cell reactor, a gas-lift reactor, a bubble column reactor (BCR), a membrane reactor, such as a Hollow. Fibre Membrane Bioreactor (HFMBR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is preferably a gaseous substrate containing CO. The gaseous substrate may be a CO-containing waste gas obtained as a by-product of an industrial process, or from some another source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Alternatively, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

The CO-containing substrate will typically contain a major proportion of CO, such as at least about 20% to about 100% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present.

While it is not necessary for the gaseous substrate to contain any hydrogen, the presence of $H_2$ should not be detrimental to product formation in accordance with methods of the invention. In particular embodiments, the presence of hydrogen results in an improved overall efficiency of alcohol production. The gaseous substrate may also contain some $CO_2$ for example, such as about 1% to about 80% $CO_2$ by volume, or 1% to about 30% $CO_2$ by volume.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; *Applied Biochemistry and Biotechnology Volume* 101, Number 3/October, 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201 and WO2009/113878, referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO2007/117157, WO2008/115080 and WO2009/022925. The optimum reaction conditions will depend partly on the particular micro-organism used. However, in general, it may be preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080, WO2009/022925, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Increasing CO Uptake

The following description focuses on application of particular embodiments of the invention to a fermentation process. However, it should be appreciated that the invention may also be more widely applicable to maintaining or increasing efficiency of growth and/or product biosynthesis of micro-organisms generally.

In accordance with the methods of the invention, there is provided a method of increasing CO-uptake of a carboxydotrophic bacteria. In particular embodiments of the invention, the method includes adding a co-factor, such as nickel, to a microbial culture such that CO-uptake increases. In particular embodiments, the co-factor is provided at a concentration higher than the nickel concentration typically provided in known systems, such that CO-uptake by the carboxydotrophic bacteria increases.

Fermentation of a substrate comprising CO by carboxydotrophic micro-organisms involves providing the substrate at a desired rate and providing other required nutrients, such as nitrogen, phosphorus, potassium, sulfur, vitamins and trace metals. Typically, the micro-organisms will be suspended in a liquid nutrient media comprising one or more dissolved nutrients, while the substrate is provided in a gaseous stream. In particular embodiments, the micro-organisms may form a biofilm, however, the nutrients are similarly provided in a liquid nutrient media. In known fermentation processes of a substrate comprising CO by carboxydotrophic micro-organisms, the nickel component of a liquid nutrient media is typically in the low micro molar range, such as less than 10 μmol/L.

In particular embodiments of the invention, the nickel is provided at a concentration of at least 10 μM; or at least 50 μM; or at least 100 μM; or at least 200 μM; or at least 500 μM; or at least 1 mM; or at least 3 mM. Nickel can be provided to a liquid nutrient media comprising nutrients suitable to support microbial growth and/or product biosynthesis at concentrations of at least 2.5 mg/L; or at least 10 mg/L; or at least 100 mg/L; or at least 500 mg/L. In particular embodiments, the nickel is maintained at a concentration of at least 2.5 mg/L/ gram dry weight of microbial cells; or at least 10 mg/L/g; or at least 100 mg/L/g; or at least 500 mg/L/g.

The optimum amount of nickel provided to a fermentation process to achieve a desired result, for example increased CO uptake and/or increased growth and/or increased alcohol production can be determined experimentally. For example, a desired concentration for optimal growth can be determined by screening fermentations with varying nickel concentrations. The Examples section below provides exemplary methods for determining an optimum nickel concentration.

It is considered that the presence of additional co-factors and/or metals may influence the rate at which carboxydotrophic bacteria can utilise a substrate comprising CO. In certain embodiments, nickel is provided in combination with other metals and/or co-factors such as Fe, Co and/or Zn. In certain embodiments, the metals and/or co-factors are provided such that the Ni:Fe ratio is at least 1:2; or at least 1:1; or at least 2:1; or at least 5:1; or at least 10:1; or at least 50:1; or at least 100:1. In certain embodiments, the metals and/or co-factors are provided such that the Ni:Co ratio is at least 1:1; or at least 2:1; or at least 5:1; or at least 10:1; or at least 50:1; or at least 100:1. In certain embodiments, the metals and/or co-factors are provided such that the Ni:Zn ratio is at least 1:1; or at least 2:1; or at least 5:1; or at least 10:1; or at least 50:1; or at least 100:1.

Carbon monoxide uptake rate correlates to growth rate of a microbial culture and/or the rate at which products such as acids and alcohols are produced. Accordingly, in particular embodiments, growth rate and/or maximum growth of a microbial culture fermenting a substrate comprising CO can be increased by providing nickel in accordance with the methods of the invention. Additionally or alternatively, the alcohol production rate and/or maximum alcohol concentration produced by a microbial culture fermenting a substrate comprising CO can be increased by providing nickel in accordance with the methods of the invention.

Additionally or alternatively, fermentation of a substrate comprising CO in accordance with the methods of the invention, results in production of alcohols, such as ethanol, without significant amounts of acids, such as acetate. As such, in certain embodiments, ethanol is the major product of the fermentation reaction, with an ethanol:acetate ratio greater than 10:1; or at least 20:1; or at least 50:1; or at least 100:1. Producing ethanol with substantially reduced amounts of acids, such as acetate has many benefits. In known systems, where acetate is produced as a significant by-product, the acetate is typically removed from a bioreactor in a continuous manner. As such, large volumes of media are required to maintain a continuous culture with a desirably low concentration of acetate. Furthermore, unless acetate can be removed from the media stream exiting the bioreactor, the used media cannot be recycled following product recovery. In particular embodiments, the invention provides a method of producing alcohols by fermentation of a substrate comprising CO, where little or no acetate is produced.

In accordance with the invention, one or more metal cofactors, such as nickel, are added to a fermentation reaction, which typically takes place in a bioreactor, at predetermined time points. It should be appreciated that the level of any one of these co-factors to be added at a particular time will depend on factors such as the time since initial inoculation of the nutrient media, the growth cycle of the micro-organisms and the rate of depletion of the metals. The cofactors may be added in salt form. Typically they will be added in the form of a composition in which it is present in combination with one or more diluents, carriers and/or other ingredients. In the simplest form of the invention, the composition consists cofactor ions/salts and water. In accordance with the invention, the addition of certain cofactors will increase the uptake of CO by the micro-organisms. In a particular form of the invention the cofactor ions are provided in nutrient media substantially matching that in the fermentation reaction (other than a relatively higher concentration of cofactor compared to other ingredients), or an alternative complementary media. The composition is preferably buffered, for example, using phosphate and/or acetate buffered to approximately pH 5.5 or 6 with aqueous base. Solutions containing the cofactor may be sterilized by autoclaving or filtration before being treated with anaerobic gas or transferred into an anaerobic atmosphere in order to remove the oxygen from these solutions.

The cofactors may be added to the fermentation reaction at any point at which one is concerned that it is depleted to the point that it may be limiting the uptake of CO in the micro-organisms. Cofactors may be added at discrete time points or continuously fed to the bioreactor at a rate calculated to ensure that the concentration in the reaction broth is within the range above mentioned.

Persons of general skill in the art will be able to calculate an appropriate rate of continuous delivery of the cofactor during the fermentation process based on observation of the average rates of alcohol production, the average rates of depletion of the cofactor, and/or on the average rate of increase in cell density, particularly having regard to the "Examples" provided herein.

As to addition of the cofactor at discrete time points, one could determine average rates of alcohol production and depletion of the cofactor as mentioned above and calculate points in the fermentation reaction at which it is most likely the cofactor will be required to be supplemented. For example, one could supplement the reaction with the cofactor continuously or at desired time points. Alternatively, one could actively monitor the fermentation process by taking samples from the bioreactor at particular time points to determine the level of the cofactor, one or more products of the fermentation reaction (for example an alcohol and/or acid) and/or cell density. The information gathered from such sampling would allow an operator to make an informed decision about the steps to take next. For example, if the level or concentration of the cofactor was low, and/or the amount of relevant fermentation products, the operator may decide to introduce additional cofactors to the bioreactor. If the concentration of the cofactor was on the higher side of the range or the level of fermentation products desirable, the operator could chose to delay supplementing the fermentation reaction.

While it is unlikely the co-factors will be depleted to any significant degree in a fermentation broth, the concentration can be maintained above a desired pre-determined level. Levels of the cofactor in the fermentation broth can be measured using methodology standard in the art. However, by way of example mass spectroscopy, inductively coupled plasma mass spectrometry, HPLC, atomic absorption mass spectroscopy or voltammetry could be used.

Cell density may be measured using standard techniques known in the art. However, by way of example, manual observation under a microscope or preferably measurement of optical density using a spectrophotometer may be used. Measurement of optical density at 600 nm ($OD_{600}$) is particularly useful.

The level of one or more fermentation products (alcohols and/or acids) can be measured using standard methodology known in the art. By way of example, these may be identified and measured using gas chromatography, high pressure liquid chromatography, enzyme-based assays or colourimetric or fluorometric assays.

The metals may be added to the bioreactor by any known means. However, by way of example solutions may be introduced into the reactor automatically through a dedicated pump or manually via septum covered port using a syringe. Additionally or alternatively, the co-factors can be added to fresh media supplied to a continuously fed bioreactor. In such embodiments, the co-factors in the fresh media supply will match the desired predetermined amount for a particular fermentation process.

Fermentation Media

In another aspect of the invention, a novel fermentation media is, provided which comprises nickel at a concentration of at least 10 µM; or at least 50 µM; or at least 100 µM; or at least 200 µM; or at least 500 µM; or at least 1 mM; or at least 3 mM. Nickel can be provided to a liquid nutrient media comprising nutrients suitable to support microbial growth and/or product biosynthesis at concentrations of at least 2.5 mg/L; or at least 10 mg/L; or at least 100 mg/L; or at least 500 mg/L. In particular embodiments, the nickel is provided at a concentration of at least 2.5 mg/L/gram dry weight of microbial cells; or at least 10 mg/L/g; or at least 100 mg/L/g; or at least 500 mg/L/g.

In another embodiment of the invention, nickel is provided in a liquid nutrient medium comprising at least Fe, Co and/or Zn. In particular embodiments, the nickel is provided such that the Ni:Fe ratio is at least 1:2; or at least 1:1; or at least 2:1; or at least 5:1; or at least 10:1; or at least 50:1; or at least 100:1. In certain embodiments, the metals and/or co-factors are provided such that the Ni:Co ratio is at least 1:1; or at least 2:1; or at least 5:1; or at least 10:1; or at least 50:1; or at least 100:1. In certain embodiments, the metals and/or co-factors are provided such that the Ni:Zn ratio is at least 1:1; or at least 2:1; or at least 5:1; or at least 10:1; or at least 50:1; or at least 100:1.

It will be appreciated that the media will be prepared using one or more nickel salts. Preferred salts include nickel chloride, nickel sulphate, nickel carbonate or nickel acetate. Similar salts of iron, cobalt and/or zinc may also be used in preparation of the media. Persons of ordinary skill in the art to which the invention relates will readily appreciate the amount of each salt required to prepare the media on the basis of the desired concentration of nickel and the molecular weight thereof.

It will be appreciated that the nutrient media will also contain other ingredients which are required or preferred for bacterial growth, as will be known in the art. Exemplary ingredients include those detailed herein after in the section entitled "Examples". Further examples are provided in U.S. Pat. Nos. 5,173,429 and 5,593,886 and WO 02/08438 referred to above.

The media may be prepared in accordance with standard procedures known in the art, as exemplified herein and in U.S. Pat. Nos. 5,173,429 and 5,593,886 and WO 02/08438. Prior to use, if required, the media can be made anaerobic using standard procedures as exemplified herein in the section headed "Examples".

The invention will now be described in more detail with reference to the following non-limiting examples.

EXAMPLES

Preparation of Media

| Media Component Examples 1-5 (LM33) | Concentration per 1.0 L of Media | Media Component Example 6 (PETC) | Concentration per 1.0 L of Media |
|---|---|---|---|
| $MgCl_2 \cdot 6H_2O$ | 0.5 g | $NH_4Cl$ | 1 g |
| NaCl | 0.2 g | KCl | 0.1 g |
| $CaCl_2 \cdot 6H_2O$ | 0.26 g | $MgSO_4 \cdot 7H_2O$ | 0.2 g |
| $NaH_2PO_4$ | 2.04 g | NaCl | 0.8 g |
| KCl | 0.15 g | $KH_2PO_4$ | 0.1 g |
| $NH_4Cl$ | 2.5 g | $CaCl_2$ | 0.02 g |
| Composite trace metal solution | 10 mL | Composite trace metal solution | 10 ml |
| Composite B vitamin solution | 10 mL | Composite B vitamin solution | 10 ml |
| Resazurin (2 g/L stock) | 1 mL | Yeast Extract | 1 g |
| $FeCl_3$ (5 g/L stock) | 2 mL | Resazurin (2 g/L stock) | 0.5 ml |
| Cysteine HCl | 0.5 g | $NaHCO_3$ | 2 g |
| Distilled water | Up to 1 L | Distilled water | Up to 1 L |

| Composite B vitamin Solution | per L of Stock Examples 1-5 | per L of Stock Example 6 |
|---|---|---|
| Biotin | 20 mg | 2 mg |
| Folic acid | 20 mg | 2 mg |
| Pyridoxine hydrochloride | 10 mg | 10 mg |
| Thiamine·HCl | 50 mg | 5 mg |
| Riboflavin | 50 mg | 5 mg |
| Nicotinic acid | 50 mg | 5 mg |
| Calcium D-(*)-pantothenate | 50 mg | 5 mg |
| Vitamin B12 | 50 mg | 0.1 mg |
| p-Aminobenzoic acid | 50 mg | 5 mg |
| Thioctic acid | 50 mg | 5 mg |
| Distilled water | To 1 L | To 1 L |

| Composite trace metal solution | per L of stock Examples 1-5 | per L of stock Example 6 |
|---|---|---|
| Nitrilotriacetic Acid | 1.5 g | 2 g |
| $MgSO_4 \cdot 7H_2O$ | 3.0 g | — |
| $MnSO_4 \cdot H_2O$ | 0.5 g | 1 g |
| NaCl | 1.0 g | — |
| $FeSO_4 \cdot 7H_2O$ | 0.1 g | — |
| $Fe(SO_4)_2(NH_4)_2 \cdot 6H_2O$ | 0.8 g | 0.8 g |
| $CoCl_2 \cdot 6H_2O$ | 0.2 g | 0.2 g |
| $ZnSO_4 \cdot 7H_2O$ | 0.2 g | 0.2 mg |
| $CuCl_2 \cdot 2H_2O$ | 0.02 g | 0.02 g |
| $AlK(SO_4)_2 \cdot 12H_2O$ | 0.02 g | — |
| $H_3BO_3$ | 0.3 g | — |
| $NaMoO_4 \cdot 2H_2O$ | 0.03 g | 0.02 g |
| $Na_2SeO_3$ | 0.02 g | 0.02 g |
| $NiCl_2 \cdot 6H_2O$ | 0.02 g | 0.02 g |
| $Na_2WO_4 \cdot 2H_2O$ | 0.02 g | 0.02 g |
| Distilled water | To 1 L | To 1 L |

Media Preparation Examples 1-5

A preparation of media at pH 5.5 was prepared as follows. All ingredients with the exception of cysteine-HCL were mixed in 400 ml dH2O. This solution was made anaerobic by heating to boiling and allowing it to cool to room temperature under a constant flow of 95% CO, 5% CO2 gas. Once cool, the cysteine HCL was added and the pH of the solution adjusted to 5.5 before making the volume up to 1000 ml; anaerobicity was maintained throughout the experiments.

Media Preparation Example 6

All media ingredients were dissolved in 1 L $dH_2O$ and pH was adjusted to 5.5 with HCl. Afterwards the medium was boiled, dispensed under 95% CO/5% $CO_2$ gas, and autoclaved at 121° C. for 15 min. Shortly before use, a sterile stock solution of reducing agents Cysteine-HCl (4.0 g/l) and $Na_2S$ (4.0 g/l) was added in a total concentration of 0.006% (w/v).

Preparation of Cr (II) Solution

A 1 L three necked flask is fitted with a gas tight inlet and outlet to allow working under inert gas and subsequent transferring of the desired product into a suitable storage flask. The flask is charged with 40 g (0.15 mol) CrC13.6H20, 18.3 g 20 mesh Zinc granules (0.28 mol) and 13.55 g or 1 mL Hg (0.0676 mol) and 500 mL of distilled water. After the flask has been flushed with N2 for one hour, the mixture is warmed to about 80° C. to initiate the reaction. Following two hours of stirring under a constant N2 flow, the mixture is continuously stirred for another 48 hours at room temperature until the reaction mixture has been converted to a deep blue solution. The solution is transferred into N2 purged serum bottles and stored in the fridge.

Preparation of Metal Solution Examples 1-5

Metal salts used are FeCl3, CoCl2.6H2O, and NiCl2.6H2O. Each metal salt is added to a serum bottle containing 50 ml water to make a 0.1M stock solution. N2 was bubbled through the solution for 30 minutes and then the bottles autoclaved. Stock solutions were then kept anaerobically to be added to the media.

Preparation of Metal Solution Example 6

To obtain different nickel concentrations during growth experiments, a nickel stock solution containing 11.8 g/L $NiCl_2$ was prepared and autoclaved at 121° C. for 15 min.

Microorganisms

Examples 1-5

The *Clostridium autoethanogenum* used is that deposited at the German Resource Centre for Biological Material (DSMZ) and allocated the accession number 19630.

Example 6

*Clostridium autoethanogenum* DSM10061, *Clostridium carboxidivorans* DSM15243, and *Clostridium ljungdahlii* DSM13528 were obtained from DSMZ (Deutsche Sammlung von Mikroorganismen and Zellkulturen GmbH).
Sampling and Analytical Procedures:

Media samples were taken from the fermentation reactions at desired time points. Each time the media was sampled, care was taken to ensure that no gas was allowed to enter into or escape from the reactor.

To determine the cell density in these experiments, the absorbance of the samples was measured at 600 nm (spectrophotometer) and the dry mass determined by extrapolation.
HPLC:

High Performance Liquid Chromatography (HPLC) was used to characterize the level of substrates and products such as for acetate, ethanol, fructose, xylose and pyruvate. HPLC System Agilent 1100 Series. Mobile Phase: 0.0025N Sulphuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for sample preparation: 400 μL of sample+50 μL of 0.15M $ZnSO_4$+50 μL of 0.15M $Ba(OH)_2$ into an Eppendorf tube. Centrifuge 10 min at 12,000 rpm, 4° C. Transfer 200 μL supernatant into an HPLC vial and inject into the HPLC instrument 5 μL.

Example 1

Effect of Selected Metals on Fermentation Products

Sterile 234 ml serum bottles were purged three times with 95% CO, 5% $CO_2$ gas and then evacuated to a vacuum of −5 psi. The serum bottles were charged with 25 ml of LM33 media and Cr(II) solution added (final concentration 0.4 mM). FeCl3, NiCl2 and CoCl2 solutions were optionally added to the serum bottles (to final concentrations of 1 mM, 0.5 mM and 0.5 mM respectively) which were inoculated with 2 ml of an actively growing *Clostridium autoethanogenum* culture from a continuous bioreactor. The headspace of the serum bottle was then filled with CO containing gas to 30 psi (composition 50% CO; 20% CO2; 3% H2; 27% N2). The serum bottles were incubated at 37° C. and continuously agitated. Samples were taken at intervals and the headspace was purged and refreshed up to 30 psi following sampling.

Results: Table 1 highlights the metabolite concentrations of the above fermentation reactions over several days.

TABLE 1

Comparison of acetate and ethanol production by *C. auto* in the presence of selected metals.

| | LM33 (control) | | | LM33 + additional Ni, Co, Fe | | |
|---|---|---|---|---|---|---|
| Time (h) | 20 | 50 | 80 | 20 | 50 | 80 |
| Acetate (g/l) | 0 | 2 | 2.7 | 0 | 1 | 1.5 |
| Ethanol (g/l) | 0 | 0.5 | 0.7 | 0 | 1 | 3.3 |

LM33 contains nickel at a concentration of approximately 1 μM. Other known media, used in the fermentation of a substrate comprising CO contain nickel concentrations up to approximately 8 μM. Clearly, at this relatively low nickel concentration, acetate is the major product. However, when the media is provided with additional nickel, cobalt and iron, the total metabolites (acetate and ethanol) increase by approximately 50%. Furthermore, the metals also have a stimulatory effect on ethanol production, increasing overall production 5-fold over 80 hours.

Example 2A

Effect of Nickel Concentration on Growth and Metabolite Production

Sterile 234 ml serum bottles were purged three times with 95% CO, 5% $CO_2$ gas and then evacuated to a vacuum of −5 psi. The serum bottles were charged with 25 ml of LM33 media. Additional NiCl2 solutions were optionally added to the serum bottle (to final concentrations of 0.1 mM and 1 mM) which were inoculated with 1 ml of an actively growing *Clostridium autoethanogenum* culture 19630 from a continuous bioreactor. The headspace of the serum bottle was then filled with CO containing gas to 30 psi (composition 100% CO). The serum bottles were incubated at 37° C. and continuously agitated. Samples were taken at intervals and the headspace was purged and refreshed up to 30 psi following sampling.

Results: Table 2 highlight rates of microbial growth and metabolite production at different nickel concentration.

TABLE 2

Comparison of microbial growth and metabolite production
by *C. auto* in presence of varying levels of nickel.

| | Additional Nickel Concentration | | | | | | | | |
|---|---|---|---|---|---|---|---|---|---|
| | 0 mM | | | 0.1 mM | | | 1 mM | | |
| Time (h) | 18 | 30 | 80 | 18 | 30 | 80 | 18 | 30 | 80 |
| Cell Density (g/L) | 0.07 | 0.11 | 0.46 | 0.14 | 0.54 | 1.08 | 0.18 | 0.59 | 1.23 |
| Acetate (g/L) | 0.53 | 0.69 | 0.50 | 0.57 | 0.61 | 0.38 | 0.48 | 0.85 | 0.66 |
| Ethanol (g/L) | 0.11 | 0.36 | 1.83 | 0.37 | 2.63 | 7.14 | 0.47 | 2.59 | 9.04 |

The control fermentation, without additional nickel grows to a total microbial cell density of approximately 0.5 g/L, whereas at elevated nickel concentrations (0.1 mM and 1 mM above LM33), the cell density increases to 1.1 ad 1.2 g/L respectively. Furthermore, total metabolite productivity is also enhanced at elevated nickel concentrations. In addition, the ethanol:acetate ratio clearly shifts towards favouring ethanol at elevated nickel concentrations. In the case of 0.1 mM concentration Ni, the ethanol:acetate ratio is approximately 19:1 (v/v) at 30 hours. This equates to an approximately 23:1 molar ratio.

Example 2B

Effect of Nickel Concentration on Growth and Metabolite Production

Sterile 234 ml serum bottles were purged three times with 95% CO, 5% $CO_2$ gas and then evacuated to a vacuum of −5 psi. The serum bottles were charged with 25 ml of LM33 media. NiCl2 solution (to final concentrations of 1 mM) and fructose (3 g/L) were added to the serum bottle which was inoculated with 1 ml of an actively growing *Clostridium autoethanogenum* culture 19630 from a continuous bioreactor. The headspace of the serum bottle was then filled with CO containing gas to 30 psi (composition 100% CO). The serum bottles were incubated at 37° C. and continuously agitated. Samples were taken at intervals and the headspace was purged and refreshed up to 30 psi following sampling.

Results: Table 3 shows microbial growth and metabolite production from substrates comprising CO and fructose over time.

TABLE 3

Microbial growth and metabolite production by
*C. auto* in presence of CO and fructose.

| | Time after inoculation (h) | | | | |
|---|---|---|---|---|---|
| | 12 | 18 | 30 | 80 | 96 |
| Cell density (g/l) | 0.16 | 0.20 | 0.73 | 0.98 | 1.07 |
| Acetic Acid g/l | 0.42 | 0.48 | 0.45 | 0.38 | 0.31 |
| Ethanol g/l | 0.25 | 0.61 | 4.19 | 7.60 | 7.81 |
| Fructose g/l | 2.87 | 2.4 | 0 | 0 | 0 |

In the presence of additional substrates, such as fructose, elevated nickel concentrations provide favourable ethanol:acetate product ratios. During the earlier stages of the fermentation reaction (up to 30 h), fructose is consumed and the ethanol to acetate product ratio exceeds 9:1. However, on complete consumption of fructose, (30 h onwards), the ethanol:acetate ratio increases to at least 25:1 (v/v) or at least 30:1 (molar ratio).

Example 4

Effect of Ni on Gas Consumption

Sterile 234 ml serum bottles were purged three times with 95% CO, 5% $CO_2$ gas and then evacuated to a vacuum of −5 psi. The serum bottles were charged with 25 ml of LM33 media. NiCl2 solution (to final concentrations of 1 mM), fructose (30 g/L) and yeast extract (5 g/L) were optionally added to the serum bottle and the serum bottles autoclaved. Cr(II) solution was optionally added to the serum bottles (final concentration 0.4 mM) which were inoculated with 1 ml of an actively growing *Clostridium autoethanogenum* culture 19630 from a continuous bioreactor. The headspace of the serum bottle was then filled with CO containing gas to 30 psi (composition 100% CO). The serum bottles were incubated at 37° C. and continuously agitated. Samples were taken at intervals and the headspace was purged and refreshed up to 30 psi following sampling.

Results: Table 4 compares microbial growth and metabolite production of fermentation reactions utilising an enriched fructose/yeast extract (FYE) substrate in addition to a substrate comprising CO.

TABLE 4

Comparison of CO uptake and metabolite production by *C. auto*
in enriched media in presence of different nickel concentrations.

| | Time (h) | Cell Density (g/L) | Acetate (g/L) | Ethanol (g/L) | Over-pressure (psi) | CO partial pressure (psi) |
|---|---|---|---|---|---|---|
| LM33FYE | 18 | 0.70 | 1.10 | 0.24 | 33* | 33 |
| | 30 | 1.31 | 0.12 | 5.32 | 32 | 20.5 |
| LM33FYE + 1 mM NiCl + Cr(II) | 18 | 0.77 | 2.42 | 1.17 | 33* | 33 |
| | 30 | 1.70 | 5.69 | 5.45 | 14 | 0.1 |

Note:
asterisk indicates pressure following regassing following sampling.

At 18 hours, both fermentation reactions are in similar stages of growth (cell density approximately 0.7-0.8 g/L). During the next 12 hours, the biomass of the control fermentation (without additional nickel) increases by a further 90%. However, the reaction comprising additional nickel increases by approximately 120%. Surprisingly, during this time, the control fermentation consumes just over 10 g/L fructose, and small amounts of CO. However, the reaction containing additional nickel consumes far less fructose (approx 5 g/L) but consumes substantially all available CO.

During this time, the reaction containing additional nickel also produces over 80% more metabolites (7.6 g/L acetate+ethanol as opposed to 4.1 g/L in the reaction without additional nickel). These results show that the additional nickel increases CO uptake thus increasing overall growth and growth rate and metabolite production.

Example 5

Effect of Ni Concentration on Microbial Growth

Media containing LM33 plus additional nickel (1 mM NiCl2) was serially diluted across a 96 weliplate into LM33 to a volume of 1 mL/well, to give the indicated additional nickel concentrations (see Table 5). Each well was inoculated with 50 μL of an actively growing *Clostridium autoethanogenum* culture 19630 from a continuous bioreactor. The wells were then mixed thoroughly and 200 ul from each well was added to a 96 well tissue culture plate. The plate was then sealed with a gas permeable sealing film and placed into an anaerobic pressure vessel. This vessel was pressurized to 30 psi with 100% CO gas and placed on an orbital shaker (150 rpm) in an incubated chamber at 37° C. Samples were analyzed at 54 hours after incubation.

Results: Table 5 compares growth rate and/or final growth density of *C. auto* as a function of increasing nickel concentration (in addition to the background level of Ni in LM33). Increasing nickel concentration (to LM33+800 μM) increases microbial growth.

Example 6

Effect of Ni Concentration on Microbial Growth in 3 Clostridia Bacteria

To test the effect of nickel on a range of acetogenic bacteria such as *Clostridium autoethanogenum* DSM10061, *Clostridium carboxidivorans* DSM15243, and *Clostridium ljungdahlii* DSM13528, growth experiments were carried out in sterile 234 ml serum bottles which were purged three times with 95% CO, 5% $CO_2$ gas and then evacuated to a vacuum of −5 psi. The serum bottles were charged with 50 mL PETC media containing different concentrations of nickel chloride (1 μM, 200 μM, 400 μM, 700 μM, and 1000 μM) and inoculated with inoculums from the same pre-culture. The serum bottles were charged with CO containing gas (2% H2; 30% N2; 47% CO; 21% CO2) to an overpressure of 30 psi. The gas was purged and refreshed at time=54 h. Growth was monitored by measuring the optical density at 600 nm ($OD_{600nm}$) and metabolites were detected by HPLC.

Results: Table 6 shows microbial growth and metabolite production of *Clostridium* autoethanogenum (DSM10061) at different nickel concentration. Table 7 shows microbial growth and metabolite production of *Clostridium carboxidivorans* (DSM15243) at different nickel concentration. Table 8 shows microbial growth and metabolite production of *Clostridium ljungdahlii* (DSM13528) at different nickel concentration. In all three fermentations, increasing nickel concentration increases microbial growth and ethanol production.

TABLE 5

Comparison of microbial growth of *C. auto* in presence of increasing concentrations of nickel.

| | Additional Nickel concentration (μM) | | | | | | | | | | |
|---|---|---|---|---|---|---|---|---|---|---|---|
| | 0 | 100 | 200 | 300 | 400 | 500 | 600 | 700 | 800 | 900 | 1000 |
| Cell density (g/L) | 0.22 | 0.23 | 0.25 | 0.28 | 0.30 | 0.35 | 0.31 | 0.37 | 0.45 | 0.43 | 0.39 |

TABLE 6

Comparison of microbial growth and metabolite production of *C. autoethanogenum* (DSM10061) in presence of increasing concentrations of nickel

| Nickel [μM] | | Time [h] | | | | |
|---|---|---|---|---|---|---|
| | | 0 | 30 | 54 | 102 | 127 |
| 0 | $OD_{600\,nm}$ | 0.009 ± 0.001 | 0.034 ± 0.001 | 0.082 ± 0.002 | 0.164 ± 0.021 | 0.199 ± 0.026 |
| | Acetate [g/l] | n.d. | n.d. | 0.23 ± 0.01 | 0.85 ± 0.10 | 1.04 ± 0.10 |
| | Ethanol [g/l] | 0.19 ± 0.02 | 0.20 ± 0.01 | 0.17 ± 0.01 | 0.19 ± 0.01 | 0.19 ± 0.01 |
| 200 | $OD_{600\,nm}$ | 0.009 ± 0.001 | 0.038 ± 0.010 | 0.052 ± 0.022 | 0.223 ± 0.141 | 0.333 ± 0.131 |
| | Acetate [g/l] | n.d. | n.d. | 0.12 ± 0.02 | 0.83 ± 0.53 | 1.48 ± 0.54 |
| | Ethanol [g/l] | 0.22 ± 0.02 | 0.22 ± 0.03 | 0.23 ± 0.03 | 0.23 ± 0.01 | 0.30 ± 0.19 |
| 400 | $OD_{600\,nm}$ | 0.010 ± 0.001 | 0.065 ± 0.002 | 0.087 ± 0.011 | 0.337 ± 0.129 | 0.452 ± 0.200 |
| | Acetate [g/l] | n.d. | n.d. | 0.18 ± 0.10 | 1.05 ± 0.85 | 1.44 ± 0.83 |
| | Ethanol [g/l] | 0.22 ± 0.02 | 0.22 ± 0.02 | 0.21 ± 0.02 | 0.68 ± 0.41 | 0.68 ± 0.21 |
| 700 | $OD_{600\,nm}$ | 0.011 ± 0.001 | 0.238 ± 0.023 | 0.292 ± 0.013 | 0.714 ± 0.060 | 0.620 ± 0.021 |
| | Acetate [g/l] | n.d. | n.d. | 0.25 ± 0.01 | 0.94 ± 0.14 | 0.95 ± 0.16 |
| | Ethanol [g/l] | 0.23 ± 0.03 | 0.24 ± 0.02 | 0.25 ± 0.03 | 0.73 ± 0.05 | 0.72 ± 0.03 |
| 1000 | $OD_{600\,nm}$ | 0.010 ± 0.001 | 0.268 ± 0.080 | 0.389 ± 0.071 | 0.720 ± 0.105 | 0.674 ± 0.098 |
| | Acetate [g/l] | n.d. | n.d. | 0.38 ± 0.01 | 1.57 ± 0.21 | 1.78 ± 0.11 |
| | Ethanol [g/l] | 0.29 ± 0.04 | 0.28 ± 0.02 | 0.26 ± 0.03 | 1.02 ± 0.09 | 0.99 ± 0.11 |

(n.d. = not detected).

TABLE 7

Comparison of microbial growth and metabolite production of C. carboxydivorans (DSM15243) in presence of increasing concentrations of nickel

| Nickel [μM] | | \ Time [h] 0 | 30 | 54 | 102 | 127 |
|---|---|---|---|---|---|---|
| 0 | $OD_{600\ nm}$ | 0.009 ± 0.001 | 0.165 ± 0.003 | 0.181 ± 0.006 | 0.187 ± 0.002 | 0.186 ± 0.006 |
| | Acetate [g/l] | n.d. | 0.48 ± 0.01 | 0.50 ± 0.01 | 0.53 ± 0.01 | 0.73 ± 0.06 |
| | Ethanol [g/l] | 0.21 ± 0.02 | 0.19 ± 0.01 | 0.19 ± 0.01 | 0.18 ± 0.02 | 0.17 ± 0.01 |
| 200 | $OD_{600\ nm}$ | 0.010 ± 0.001 | 0.185 ± 0.052 | 0.239 ± 0.028 | 0.274 ± 0.025 | 0.285 ± 0.046 |
| | Acetate [g/l] | n.d. | 0.37 ± 0.13 | 0.38 ± 0.02 | 0.43 ± 0.09 | 0.61 ± 0.02 |
| | Ethanol [g/l] | 0.18 ± 0.01 | 0.18 ± 0.01 | 0.33 ± 0.02 | 0.33 ± 0.19 | 6.69 ± 0.08 |
| 400 | $OD_{600\ nm}$ | 0.011 ± 0.002 | 0.271 ± 0.001 | 0.310 ± 0.037 | 0.304 ± 0.035 | 0.291 ± 0.026 |
| | Acetate [g/l] | n.d. | 0.35 ± 0.02 | 0.41 ± 0.02 | 0.37 ± 0.19 | 0.47 ± 0.03 |
| | Ethanol [g/l] | 0.18 ± 0.06 | 0.33 ± 0.11 | 0.75 ± 0.01 | 0.86 ± 0.03 | 0.89 ± 0.08 |
| 700 | $OD_{600\ nm}$ | 0.010 ± 0.001 | 0.402 ± 0.014 | 0.689 ± 0.097 | 0.519 ± 0.078 | 0.584 ± 0.088 |
| | Acetate [g/l] | n.d. | 0.34 ± 0.01 | 0.40 ± 0.05 | 0.65 ± 0.06 | 0.63 ± 0.32 |
| | Ethanol [g/l] | 0.20 ± 0.01 | 0.27 ± 0.01 | 0.84 ± 0.03 | 0.86 ± 0.25 | 1.01 ± 0.17 |
| 1000 | $OD_{600\ nm}$ | 0.009 ± 0.001 | 0.705 ± 0.014 | 1.058 ± 0.006 | 0.943 ± 0.002 | 0.981 ± 0.088 |
| | Acetate [g/l] | n.d. | 0.29 ± 0.04 | 0.39 ± 0.02 | 0.62 ± 0.21 | 0.47 ± 0.11 |
| | Ethanol [g/l] | 0.18 ± 0.01 | 0.44 ± 0.09 | 0.74 ± 0.05 | 0.88 ± 0.03 | 1.04 ± 0.02 |

(n.d. = not detected).

TABLE 8

Comparison of microbial growth and metabolite production of Clostridium ljungdahlii (DSM13528) in presence of increasing concentrations of nickel

| Nickel [μM] | | \ Time [h] 0 | 30 | 54 | 102 | 127 |
|---|---|---|---|---|---|---|
| 0 | $OD_{600\ nm}$ | 0.010 ± 0.001 | 0.049 ± 0.004 | 0.135 ± 0.052 | 0.262 ± 0.035 | 0.345 ± 0.002 |
| | Acetate [g/l] | n.d. | 0.03 ± 0.03 | 0.26 ± 0.01 | 0.80 ± 0.33 | 1.20 ± 0.32 |
| | Ethanol [g/l] | 0.25 ± 0 | 0.24 ± 0.01 | 0.26 ± 0.02 | 0.32 ± 0.05 | 0.36 ± 0.06 |
| 200 | $OD_{600\ nm}$ | 0.010 ± 0.001 | 0.057 ± 0.003 | 0.163 ± 0.053 | 0.273 ± 0.001 | 0.284 ± 0.016 |
| | Acetate [g/l] | n.d. | 0.07 ± 0.07 | 0.24 ± 0.10 | 0.38 ± 0.10 | 0.77 ± 0.24 |
| | Ethanol [g/l] | 0.23 ± 0.02 | 0.23 ± 0.02 | 0.27 ± 0.03 | 0.57 ± 0.11 | 0.58 ± 0.07 |
| 400 | $OD_{600\ nm}$ | 0.011 ± 0.002 | 0.097 ± 0.024 | 0.114 ± 0.030 | 0.199 ± 0.103 | 0.310 ± 0.017 |
| | Acetate [g/l] | n.d. | n.d. | 0.15 ± 0.04 | 0.20 ± 0.01 | 0.30 ± 0.19 |
| | Ethanol [g/l] | 0.22 ± 0.02 | 0.22 ± 0.01 | 0.21 ± 0.02 | 0.53 ± 0.31 | 0.77 ± 0.24 |
| 700 | $OD_{600\ nm}$ | 0.009 ± 0.001 | 0.235 ± 0.076 | 0.427 ± 0.182 | 0.579 ± 0.062 | 0.528 ± 0.054 |
| | Acetate [g/l] | n.d. | n.d. | 0.21 ± 0.05 | 0.24 ± 0.03 | 0.34 ± 0.16 |
| | Ethanol [g/l] | 0.25 ± 0.01 | 0.24 ± 0.01 | 0.35 ± 0.11 | 0.73 ± 0.01 | 0.82 ± 0.03* |
| 1000 | $OD_{600\ nm}$ | 0.011 ± 0.001 | 0.549 ± 0.049 | 0.691 ± 0.017 | 0.862 ± 0.324 | 0.853 ± 0.329 |
| | Acetate [g/l] | n.d. | n.d. | 0.23 ± 0.02 | 0.31 ± 0.03 | 0.46 ± 0.03 |
| | Ethanol [g/l] | 0.24 ± 0.01 | 0.26 ± 0.01 | 0.42 ± 0.14 | 0.68 ± 0.26 | 0.98 ± 0.11 |

(n.d. = not detected).

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including; but not limited to".

What we claim is:

1. A method of producing at least one product selected from the group consisting of acids, alcohols and mixtures thereof by microbial fermentation, the method comprising:
   providing a substrate comprising CO to a bioreactor comprising a culture of one or more microorganisms, and anaerobically fermenting the substrate to produce at least one product:
   wherein the culture is characterized in that it contains at least 200 μM of nickel.

2. The method according to claim 1, where both acids and alcohols are produced and the ratio of alcohols: acids is at least 10:1.

3. The method according to claim 2, where the ratio of alcohols to acids is at least 20:1.

4. The method according to claim 1 wherein the alcohol is ethanol and the acid is acetate.

5. The method according to claim 1,
   wherein the nickel is added to the culture as an aqueous solution of a compound selected from the group consisting of nickel chloride, nickel sulphate, nickel carbonate, nickel acetate and mixtures thereof.

6. The method according to claim 5, wherein the nickel compound is nickel chloride.

7. The method according to claim 1 wherein the nickel is present at a concentration from 200 µM to 1 mM.

8. The method according to claim 1, wherein the nickel is present at a concentration from 300 µM to 1 mM.

9. The method according to claim 1, wherein the nickel is present at a concentration from 400 µM to 1 mM.

10. The method according to claim 1 wherein the substrate comprises from about 15% to about 100% CO by volume.

11. The method according to claim 10 wherein the substrate comprises from about 40% to about 70% CO by volume.

12. The method according to claim 10 wherein the substrate comprises a gas obtained from a steel mill.

13. The method according to claim 1, wherein the microorganism is selected from the group consisting of *Clostridium, Moorella, Pyrococcus, Eubacterium, Desulfobacterium, Carboxydothermus, Acetogenium, Acetobacterium, Acetoanaerobium, Butyribaceterium* and *Peptostreptococcus*.

14. The method according to claim 13, wherein the microorganism is *Clostridium autoethanogenum, Clostridium carboxydivorans* or *Clostridium ljungdahlii*.

15. The method of claim 1 where the culture further comprises iron present at a ratio of Ni:Fe from about 1:2 to about 100:1.

16. The method of claim 15 where the culture further comprises cobalt present at a ratio of Ni:Co from about 1:1 to about 100:1.

17. The method of claim 16 where the culture further comprises zinc present at a ratio of Ni:Zn from about 1:1 to about 100:1.

18. The method of claim 15 where the culture further comprises zinc present at a ratio of Ni:Zn from about 1:1 to 100:1.

19. The method of claim 1 where the culture further comprises cobalt present at a ratio of Ni:Co from about 1:1 to about 100:1.

20. The method of claim 1 where the culture further comprises zinc present at a ratio of Ni:Zn from about 1:1 to about 100:1.

* * * * *